(12) United States Patent
Omr et al.

(10) Patent No.: US 10,267,646 B2
(45) Date of Patent: Apr. 23, 2019

(54) METHOD AND SYSTEM FOR VARYING STEP LENGTH ESTIMATION USING NONLINEAR SYSTEM IDENTIFICATION

(71) Applicant: Trusted Positioning, Inc., Calgary (CA)

(72) Inventors: Medhat Omr, Calgary (CA); Ahmed Wahdan, Calgary (CA); Jacques Georgy, Calgary (CA); Aboelmagd Noureldin, Calgary (CA)

(73) Assignee: InvenSense, Inc., San Jose, CA (US)

( * ) Notice: Subject to any disclaimer, the term of this patent is extended or adjusted under 35 U.S.C. 154(b) by 540 days.

(21) Appl. No.: 14/764,519

(22) PCT Filed: Jan. 30, 2014

(86) PCT No.: PCT/CA2014/000060
§ 371 (c)(1),
(2) Date: Jul. 29, 2015

(87) PCT Pub. No.: WO2014/117252
PCT Pub. Date: Aug. 7, 2014

(65) Prior Publication Data
US 2015/0362330 A1    Dec. 17, 2015

Related U.S. Application Data

(60) Provisional application No. 61/759,522, filed on Feb. 1, 2013.

(51) Int. Cl.
*G01C 22/00* (2006.01)
*G01C 21/14* (2006.01)
(Continued)

(52) U.S. Cl.
CPC ............ *G01C 22/006* (2013.01); *A61B 5/112* (2013.01); *A61B 5/725* (2013.01); *G01C 21/14* (2013.01);
(Continued)

(58) Field of Classification Search
CPC ....... G01C 22/006; G01C 21/14; A61B 5/112; A61B 5/725; A61B 2562/0219
(Continued)

(56) References Cited

U.S. PATENT DOCUMENTS 5,991,525 A * 11/1999 Shah ................... G05B 13/04
 700/29
9,392,966 B2 * 7/2016 Ten Kate ............. A61B 5/1117
(Continued)

*Primary Examiner* — Sujoy K Kundu
*Assistant Examiner* — Lynda Dinh
(74) *Attorney, Agent, or Firm* — Bay Area Technology Law Group PC

(57) ABSTRACT

The present disclosure relates to a method and system for estimating varying step length for on foot motion (such as for example walking or running). The present method and apparatus is able to be used in anyone or both of two different phases depending on the embodiment. The first phase is a model-building phase done offline to obtain the nonlinear model for the step length as a function of different parameters that represent human motion dynamics, the model is built using a nonlinear system identification technique. In the second phase the nonlinear model is used to calculate the step length from the different parameters that represent human motion dynamics used as input to the model. These parameters are obtained from sensors readings from the sensors in the apparatus. This second phase is the more frequent usage of the present method and apparatus for a variety of applications.

19 Claims, 12 Drawing Sheets

(51) Int. Cl.
*A61B 5/11* (2006.01)
*A61B 5/00* (2006.01)

(52) U.S. Cl.
CPC ...... *A61B 2562/0219* (2013.01); *G01C 22/00* (2013.01)

(58) Field of Classification Search
USPC ........................................................ 702/160
See application file for complete search history.

(56) References Cited

U.S. PATENT DOCUMENTS

| | | | |
|---|---|---|---|
| 9,597,015 B2* | 3/2017 | McNames | A61B 5/1071 |
| 2003/0195706 A1* | 10/2003 | Korenberg | G06F 19/20 |
| | | | 702/19 |
| 2011/0208444 A1* | 8/2011 | Solinsky | A61B 5/112 |
| | | | 702/41 |
| 2013/0080255 A1* | 3/2013 | Li | G01C 22/006 |
| | | | 705/14.58 |
| 2013/0310979 A1* | 11/2013 | Herr | B62D 57/032 |
| | | | 700/258 |

* cited by examiner

METHOD AND SYSTEM FOR VARYING STEP LENGTH ESTIMATION USING NONLINEAR SYSTEM IDENTIFICATION

RELATED APPLICATIONS

This application claims the benefit of U.S. Provisional Patent Application No. 61/759,522 filed Feb. 1, 2013 which is hereby incorporated by reference.

TECHNICAL FIELD

The present disclosure relates to a method and system for tracking human movement, and more particularly for tracking individual travel by foot.

BACKGROUND

Inertial sensors (e.g. accelerometers and gyroscopes) are commonly used for tracking human movements especially for "on foot" activities (for example walking or running). Accelerometers are used for measuring a user's acceleration, from which steps can be detected and can form the basis of existing step length estimation techniques.

For on foot motion (for example walking or running), there are many methods known in literature for estimating step length. The easiest and most trivial assumption (but not accurate) is that the step length is a constant value regardless of the pedestrian characteristics like height, weight, and gender, or motion dynamics (for example walking or running speed and acceleration).

Some methods require the placement of inertial sensors on certain locations on the user's body (for example, on a foot, waist or chest . . . etc.), which again make it hard to apply these methods for a variety of applications except those supporting the location for which the method was built.

One method for step length calculation is the double integration of acceleration readings to obtain pedestrian displacement. This method, if used alone, results in lower accuracy due to the drift increasing over time and the high noise and errors in commercial accelerometer readings especially for cases with low acceleration values. The common technique to enable using this method is to restart the integration with each detected step because the velocity is zero at each footfall. This is why this technique prefers foot mounting or lower leg mounting, to avoid the body sway as this technique needs a zero velocity update at each step detection.

Other known methods may be categorized roughly into two main groups, namely methods based on biomechanical models, and methods based on empirical relationships. An example of a biomechanical model method is kneeless biped model for step length estimation, wherein, the kneeless biped is modeled as an inverted pendulum and the final estimation is scaled with some constant dependent on the user. One drawback of this method is that it is user-dependent since for this method to work properly, one must find the best scale constant for each specific user.

As another example, a biomechanical model method can assume a more complex model by considering the vertical displacement of the center of mass of the user's body through double integration of the acceleration ruled by two pendulums, namely, an inverted pendulum with the leg's length during the swing phase, and a second pendulum, during the double-stance phase of the step known as the stride length (where stride length is defined as the length of two consecutive steps). In this case, the method can be computed as the summation of the displacements in both stages. One drawback of this method is that it requires the knowledge of the foot length (from first metatarsal head to the calcaneal tuberosity) of the user, which makes it again, user-dependent/specific, and certain configurations may work with one user but not with another user because of differences in their physical characteristics like height and/or leg-to-body ratio. The same problem again appears in the empirical relationships, where one or more parameters require calibration and customization for each user. Another example of these methods is a method that develops a relationship between the stride length, the step counter, the first harmonic of the vertical acceleration of the center of mass of the person, and a constant that needs calibration. There are several other empirical methods, in some of which the equations are obtained experimentally and need calibration of parameters.

Some prior work noted that the speed of a moving pedestrian can affect his step length, for example when a person walks faster he tends to increase the length of his step; also his motion style and dynamics are affected by his increased speed. A related parameter is that the step frequency affects the step length.

In some prior work it was assumed that the step length has a linear relation with the step frequency, where step frequency indicates how many steps are detected per second. The results of this method as is are not satisfactory for applications that requires accurate varying step length estimation, as the frequency of step is not the only parameter that can affect the step length. Another technique is used to estimate step length and it is considered a modification to the previous approach that only considered the step frequency in a linear relation with step length. In this approach a linear model can be used to relate the step length with both step frequency and acceleration variance in a step where acceleration variance is the variance of the acceleration measured by the accelerometer during one step period. The parameters of the previously mentioned linear models are obtained either by online training when a GNSS signal is available or by offline training before the model is used by the user. The main drawback of online training is that the model requires training with different walking or running speeds, which is not guaranteed and most probably will not happen in a natural real-life trajectory during GNSS availability. This issue is solved in implementations which involve offline training instead, in which training data is collected before usage. The results are shown experimentally to be better than the online training implementations. In implementations that are using offline training the parameters of the linear model can be calculated using any linear identification method such as linear regression. Different users should walk with different speeds so that different values of frequency and acceleration variance can be obtained. These values can be fed to the linear regression model to calculate approximate parameters that suit a large number of users.

The main drawback in the last mentioned approach is the assumption of linear relation, which neglects the effect of some motion dynamics and speeds that differ among users and can cause the relation to be nonlinear.

Thus there is a need for a method and system capable of mitigating such problems by being able to build and/or use nonlinear model(s) for the step length as a function of the parameters representing human motion dynamics.

SUMMARY

The present disclosure relates to a method and system for estimating varying step length for "on foot" motion (for example a walking or running motion). The present method and system may be used in any one or both of two different phases. In some embodiments, the first phase is used. In some other embodiments, the second phase is used. In a third group of embodiments, the first phase is used, and then the second phase is used. The first phase is a model-building phase done offline to obtain a nonlinear model for the step length as a function of different parameters that represent human "on foot" motion dynamics. A nonlinear system identification technique may be used for building this model. In the second phase the nonlinear model is used to calculate the step length from the different parameters that represent human "on foot" motion dynamics used as input to the model. These parameters may be obtained from sensor readings from sensors in the system. This second phase is the more frequent usage of the present method and system for a variety of applications.

In an embodiment, the nonlinear system identification technique used may be Fast Orthogonal Search (FOS); it is used to build a model that can provide an accurate varying step length regardless of the user's features and the varying human motion dynamics among users. To be able to achieve a generic mathematical model using FOS, the FOS technique should be trained with a large data set of candidate data from different people that can describe different human dynamics that varies with speed and varies among users during on foot motion activities.

In some embodiments, the present method and apparatus can use vertical acceleration to detect steps and/or in calculating the parameters from the acceleration readings during the detected step. The vertical acceleration may be obtained by either: (i) a vertically mounted accelerometer if the application allows such a mounting; or (ii) the leveled vertical acceleration independent on the application and/or mounting. In the second case, pitch and roll angles can be used in levelling the accelerometer readings to obtain a leveled vertical acceleration signal. In some other embodiments, the present method and system can use the magnitude of the accelerometer readings to detect steps and/or in calculating the parameters from the acceleration readings during the detected step. In this latter case the gravity acceleration may be removed from the magnitude depending on the usage.

The present method and system can use different parameters that represent human motion dynamics. In some embodiments, the different parameters that represent human motion dynamics used are any one or any combination of the following: step frequency; acceleration variance during step; acceleration peak value during step; peak to peak acceleration value during step; among others. It has to be noted that the acceleration can be any of the options discussed in the previous paragraph. In an embodiment, the parameters that represent human motion dynamics used are step frequency and acceleration variance during step.

In some embodiments, the present method and system can be used for step length estimation for 2D motion. In other embodiments that involve 3D motion, the present method and apparatus can be used for 3D step length estimation or for estimating the 2D projection of the step length; in such cases the different parameters that represent human motion dynamics can include some parameters related to height or height changes.

In some embodiments, the inputs to the model whether in the model-building phase (first phase) or the usage phase (second phase) are the different parameters that represent human motion dynamics. In some embodiments, the inputs to the model whether in the model-building phase (first phase) or the usage phase (second phase) are the different parameters that represent human motion dynamics together with other inputs derived from some or all of these parameters such as (among others):
(i) different time-delayed versions of these parameters; and/or
(ii) different terms obtained by multiplying: (a) any/some/all of these parameters or their time-delayed versions by (b) any/some/all of these parameters or their time-delayed versions.

During the model-building phase, a group of people collect the datasets (datasets of sensor readings) used for building the model using the nonlinear system identification technique. In some embodiments, the group of pedestrians' datasets used are from different genders, and with different heights, weights, and walking and/or running styles; and this group collect the data by walking and/or running with different speeds. During model-building, with each step detected, a reference step length and the used parameters that represent human motion dynamics are collected, stored and then fed to the system identification technique.

In the more frequent usage of the present method and system, the nonlinear model is used to calculate the step length from the different parameters that represent human motion dynamics used as input to the model, wherein these parameters are obtained from sensor readings. Some applications include: (i) measuring the distance traveled during an on foot activity such as walking and/or running whether with constant or varying speeds; (ii) using Pedestrian Dead Reckoning (PDR) directly with any step detection technique and any heading source (such PDR solution can be used solely, it can be integrated with other systems that provide absolute navigational information or with other sensors or with any integrated navigation solution using any integration technique and any sensors).

The present method and system can be used in many applications. In some embodiments, the application has the system mounted on the body of, held by, or carried by a person while moving on foot, wherein the mobility of the system with respect to the person is constrained or unconstrained. The system may be tethered or non-tethered to the person's body.

In some embodiments, the application using the present method and system can use: (i) the model-building only, (ii) the already obtained model only, or (iii) both model-building then model usage.

For the model-building, in order to run the system identification technique used to build the model, any machine or device which is capable of processing can be used, where the model-building technique can be run and outputs a model for estimating the step length.

The present method and system includes at least: (i) a single axis accelerometer which is vertically mounted, or (ii) a tri-axial accelerometer (this means a triad of accelerometers). In one embodiment, the system includes at least a single axis accelerometer which is vertically mounted, which may be used as the sole sensor. In another embodiment, the system includes at least a tri-axial accelerometer, which may be used as the sole sensor. In another embodiment, the system includes at least a tri-axial accelerometer and at least a tri-axial gyroscope, which may be used as the sole sensors. In some embodiments, in addition to the above-mentioned inertial sensors, the system may include additional types of sensors, for example magnetometers, barometers or any other type of additional sensors; any of the available sensors may be used. The system may also include a source of obtaining absolute navigational information (such as GNSS, WiFi, RFID, Zigbee, Cellular based localization among others), any other positioning system, or combination of systems may be included as well. In embodiments that involve a 3D motion, where the step length estimation is for a 3D step length estimation or for estimating a 2D projection of the step length, the system additionally includes (in addition to all the above-mentioned sensor combinations for different embodiments) a means for measuring height or height changes, for example: (i) a barometer, or (ii) a source of obtaining absolute navigational information.

In some embodiments, the systems may also include processing means. In some of these embodiments, the sensors in the system are in the same module or device as the processing means. In some other embodiments, the sensors included in the system may be contained in a separate device or module other than the device or module containing the processing means; the two devices or modules may communicate through a wired or a wireless mean of communication.

In some embodiments, in the model-building, the aforementioned system (whether in one or more device(s) or module(s)) may be used for any one of the following: (i) data collection and logging (including saving or storing) while the model-building technique runs on another computing machine, (ii) data reading and processing the model-building technique, (iii) data collection, logging (including saving or storing), and processing the model-building technique.

In some embodiments, in the model usage to estimate the step length, the aforementioned system (whether in one or more device(s) or module(s)) may be used for any one of the following: (i) data collection and logging (including saving or storing) while the model for step length estimation runs on another computing machine, (ii) data reading and using the model for step length estimation, (iii) data collection, logging (including saving or storing), and using the model for step length estimation.

A method for estimating varying step length for on foot motion of a pedestrian is provided, the method including: (a) providing a device moveable with the pedestrian, the device positionable in any orientation, wherein the device comprises a sensor assembly, and wherein the sensor assembly has at least one sensor, the at least one sensor capable of providing sensor readings; (b) detecting steps from the sensor readings; (c) obtaining parameters that represent human motion dynamics from the sensor readings for the detected steps; and (d) using the parameters that represent human motion dynamics to: (i) build a step length model using a nonlinear system identification technique, (ii) utilize a step length model built using a nonlinear system identification technique to estimate step length, or (iii) build a step length model using a nonlinear system identification technique and utilize the step length model built to estimate step length.

A method for estimating varying step length for on foot motion of a pedestrian is provided, the method including: (a) providing a device moveable with the pedestrian, the device positionable in any orientation, wherein the device comprises a sensor assembly, and wherein the sensor assembly has at least one sensor, the at least one sensor capable of providing sensor readings; (b) obtaining sensor readings for a plurality of pedestrians; (c) running a step detection technique on the obtained sensor readings to detect steps; (d) obtaining parameters that represent human motion dynamics from the sensor readings for each detected step; (e) obtaining a reference step length for each detected step; (f) feeding the parameters that represent human motion dynamics and the reference step length to a nonlinear system identification technique; and (g) running the system identification technique to build a model to estimate a step length from the parameters that represent human motion dynamics.

A method for estimating varying step length for on foot motion of a pedestrian is provided, the method including: (a) providing a device moveable with the pedestrian, the device positionable in any orientation, wherein the device includes a sensor assembly, and wherein the sensor assembly has at least one sensor, said at least one sensor capable of providing sensor readings; (b) obtaining the sensor readings; (c) running a step detection technique on the sensor readings to detect a step; (d) obtaining parameters that represent human motion dynamics from the sensor readings for the detected step; and (e) passing the parameters that represent human motion dynamics to a step length model and estimating an output step length from the model, wherein the step length model was built using a nonlinear system identification technique.

The methods described above are operable with the device untethered or untethered to the pedestrian; and the nonlinear system identification technique may be Fast Orthogonal Search. The sensor may be an accelerometer or a tri-axial accelerometer. The parameters that represent human motion dynamics may be one or more of the following: step frequency, acceleration variance during step, acceleration peak value during step, or peak to peak acceleration value during step.

A system for estimating varying step length for on foot motion of a pedestrian is provided, the system including: a device moveable with the pedestrian, the device in any orientation, the device including: an assembly of sensors comprising at least one sensor, said at least one sensor capable of providing sensor readings; and a receiver for receiving absolute navigational information about the device from an external source, and producing an absolute navigational information output; and a processor, coupled to receive the sensor readings and the absolute navigational information output, and operative to: (i) detect steps from the sensor readings; (ii) obtain parameters that represent human motion dynamics from the sensor readings for the detected steps; and (iii) use the parameters that represent human motion dynamics to: (A) build a step length model using a nonlinear system identification technique, (B) utilize a step length model built using a nonlinear system identification technique to estimate step length, or (C) build a step length model using a nonlinear system identification technique and utilize the step length model to estimate step length.

A system for estimating varying step length for on foot motion of a pedestrian, the system including: a device moveable with the pedestrian, said device is in any orientation, the device including: an assembly of sensors comprising at least one sensor, said at least one sensor capable of providing sensor readings; and a receiver for receiving absolute navigational information about the device from an external source, and producing an absolute navigational information output; and a processor, coupled to receive the sensor readings and the absolute navigational information output, wherein the processor is operative to: (a) obtain the sensor readings for a plurality of pedestrians; (b) run a step detection technique on the obtained sensor readings; (c) obtain parameters that represent human motion dynamics from the sensor readings for each detected step; (d) obtain a reference step length for each detected step; (e) feed the parameters that represent human motion dynamics and the reference step length to a nonlinear system identification technique; and (g) run the system identification technique to build a model to estimate the step length from the parameters that represent human motion dynamics.

A system for estimating varying step length for on foot motion of a pedestrian, the system including: a device moveable with the pedestrian, said device is in any orientation, the device comprising an assembly of sensors, said assembly of sensors comprising at least one sensor, said at least one sensor capable of providing sensor readings; and a processor operative to: (a) obtain the sensor readings; (b) run a step detection technique on the sensor readings; (c) obtain parameters that represent human motion dynamics from the sensor readings for the detected step; and (d) pass the parameters that represent human motion dynamics to a step length model and estimating the output step length from the model, wherein the step length model was built using a system identification technique.

The device in the systems described above may be tethered or untethered to the pedestrian; and the sensor may be an accelerometer or a tri-axial accelerometer. Furthermore, the processor may be positioned within the device or be external to the device.

DETAILED DESCRIPTION

The present disclosure relates to a method and system for estimating varying step length for on foot motion (for example walking or running) of a pedestrian. In this document, a "pedestrian" is defined as a person on foot or performing on foot activities, such as, but not limited to, walking or running. The present method and system is able to be used in any one or both of two different phases. In some embodiments, the first phase is used. In other embodiments, the second phase is used. In a third group of embodiments, the first phase is used, and then the second phase is used. The first phase is a model-building phase done offline to obtain the nonlinear model for the step length as a function of different parameters that represent human motion dynamics. A nonlinear system identification technique is used for building this model. In the second phase the nonlinear model is used to calculate the step length from the different parameters that represent human motion dynamics used as input to the model. These parameters are obtained from sensor readings from the sensors in the apparatus. This second phase is the more frequent usage of the present method and system for a variety of applications.

Absolute navigational information is information related to navigation and/or positioning and is provided by "reference-based" systems that depend upon external sources of information, for example GNSS. Self-contained navigational information is information related to navigation and/or positioning and is provided by self-contained and/or "non-reference based" systems within a device/platform, and thus need not depend upon external sources of information that can become interrupted or blocked. Examples of self-contained information are readings from motion sensors such as accelerometers and gyroscopes.

Figure 1:
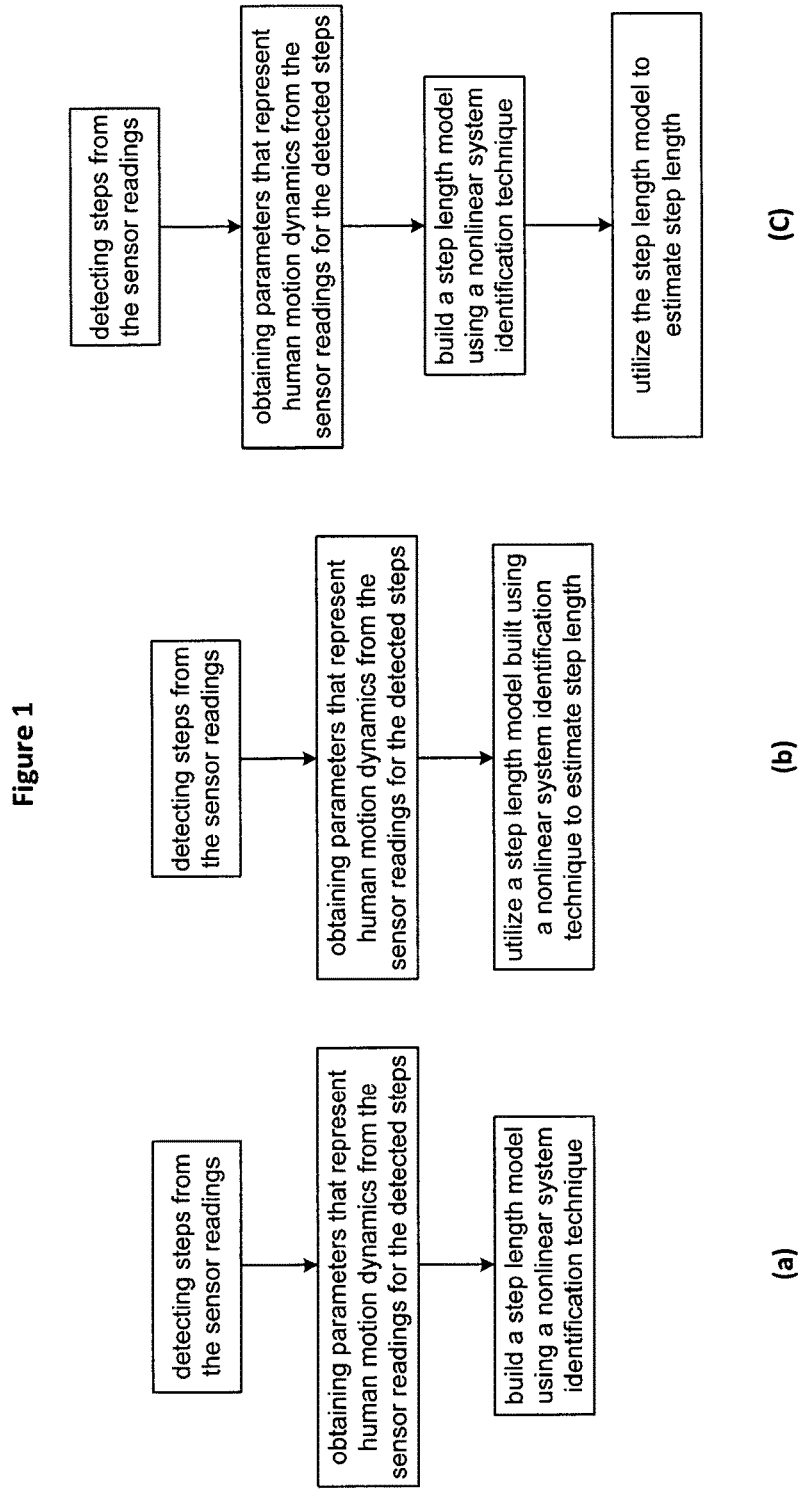
FIG. 1 is a flow chart showing: (a) an embodiment of the method using the model building phase, (b) an embodiment of the method using the model utilization phase, and (c) an embodiment of the method using both the model building phase and the model utilization phase.
Figure 2:
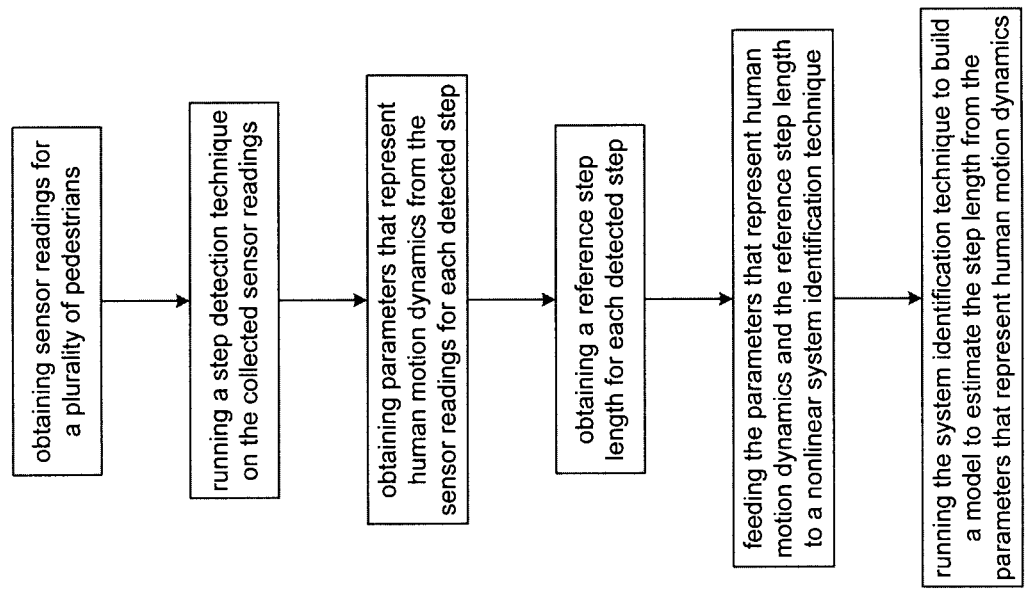
FIG. 2 is a flow chart showing an example of the steps for the model building phase.
Figure 3:
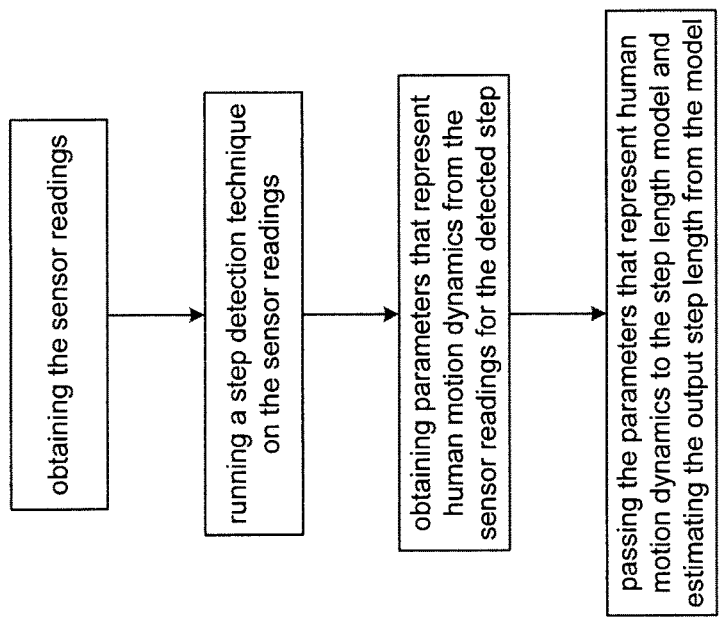
FIG. 3 is a flow chart showing an example of the steps for the model utilization phase.

Having regard to FIG. 1, the first phase, which is the model building phase, is depicted in FIG. 1 (a); the second phase, which is the model utilization phase, is depicted in FIG. 1 (b); and an embodiment using both phases is depicted in FIG. 1 (c). Having regard to FIG. 2, the steps of an embodiment of the model building phase are shown. Having regard to FIG. 3, the steps of an embodiment of the model utilization phase are shown.

Figure 4:
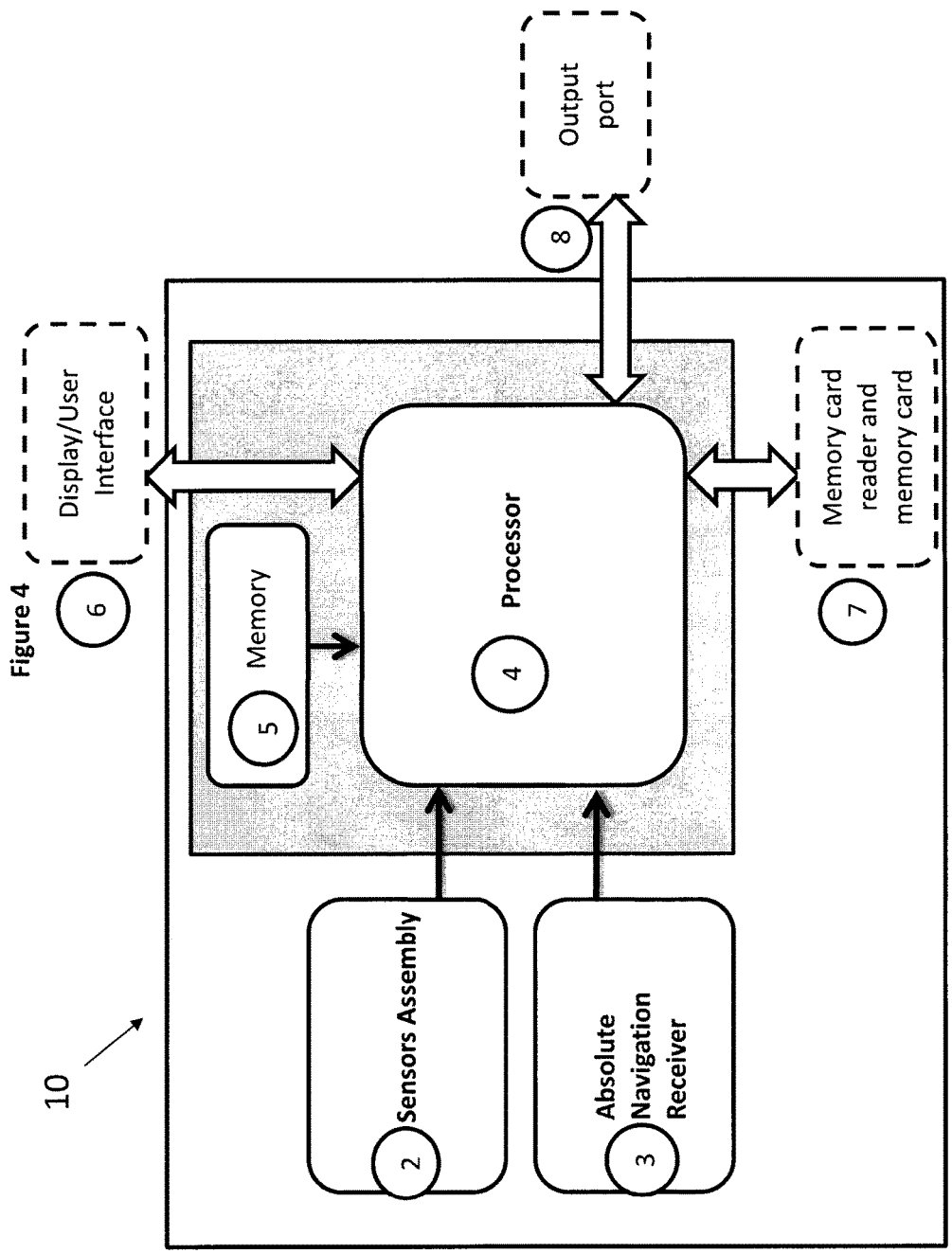
FIG. 4 is a block diagram depicting one embodiment of the device used in the model building phase.

Having regard to FIG. 4, the present device 10 may include a self-contained sensor assembly 2, capable of obtaining or generating "relative" or "non-reference based" readings relating to navigational information about the moving object, and producing an output indicative thereof. In one embodiment, the sensor assembly 2 may, for example, include at least one accelerometer, for measuring acceleration rates. In another embodiment, the sensor assembly 2 may, for example, include at least tri-axial accelerometer, for measuring acceleration rates. In yet another embodiment, the sensor assembly 2 may, optionally, include other self-contained sensors such as, without limitation, a gyroscope, for measuring turning rates of the of the device; a three dimensional (3D) magnetometer, for measuring magnetic field strength for establishing heading; a barometer, for measuring pressure to establish altitude; or any other sources of "relative" navigational information.

The present training device 10 may also include a receiver 3 capable of receiving "absolute" or "reference-based" navigation information about the device from external sources, such as satellites, whereby receiver 3 is capable of producing an output indicative of the navigation information. For example, receiver 3 may be a GNSS receiver capable of receiving navigational information from GNSS satellites and converting the information into position and velocity information about the moving object. The GNSS receiver may also provide navigation information in the form of raw measurements such as pseudoranges and Doppler shifts. The GNSS receiver might operate in one of different modes, such as, for example, single point, differential, RTK, PPP, or using wide area differential (WAD) corrections (e.g. WAAS).

In some embodiments, the present device 10 may include at least one processor 4 coupled to receive the sensor readings from the sensor assembly 2, and the absolute navigational information output from the receiver 3. In some embodiments, the present device 10 may include at least one memory 5. Optionally, the device 10 may include a display or user interface 6. It is contemplated that the display 6 may be part of the device 10, or separate therefrom (e.g., connected wired or wirelessly thereto). Optionally, the device 10 may include a memory device/card 7. It is contemplated that the memory device/card 7 may be part of the device 10, or separate therefrom (e.g., connected wired or wirelessly thereto). Optionally, the device 10 may include an output port 8.

Figure 5:
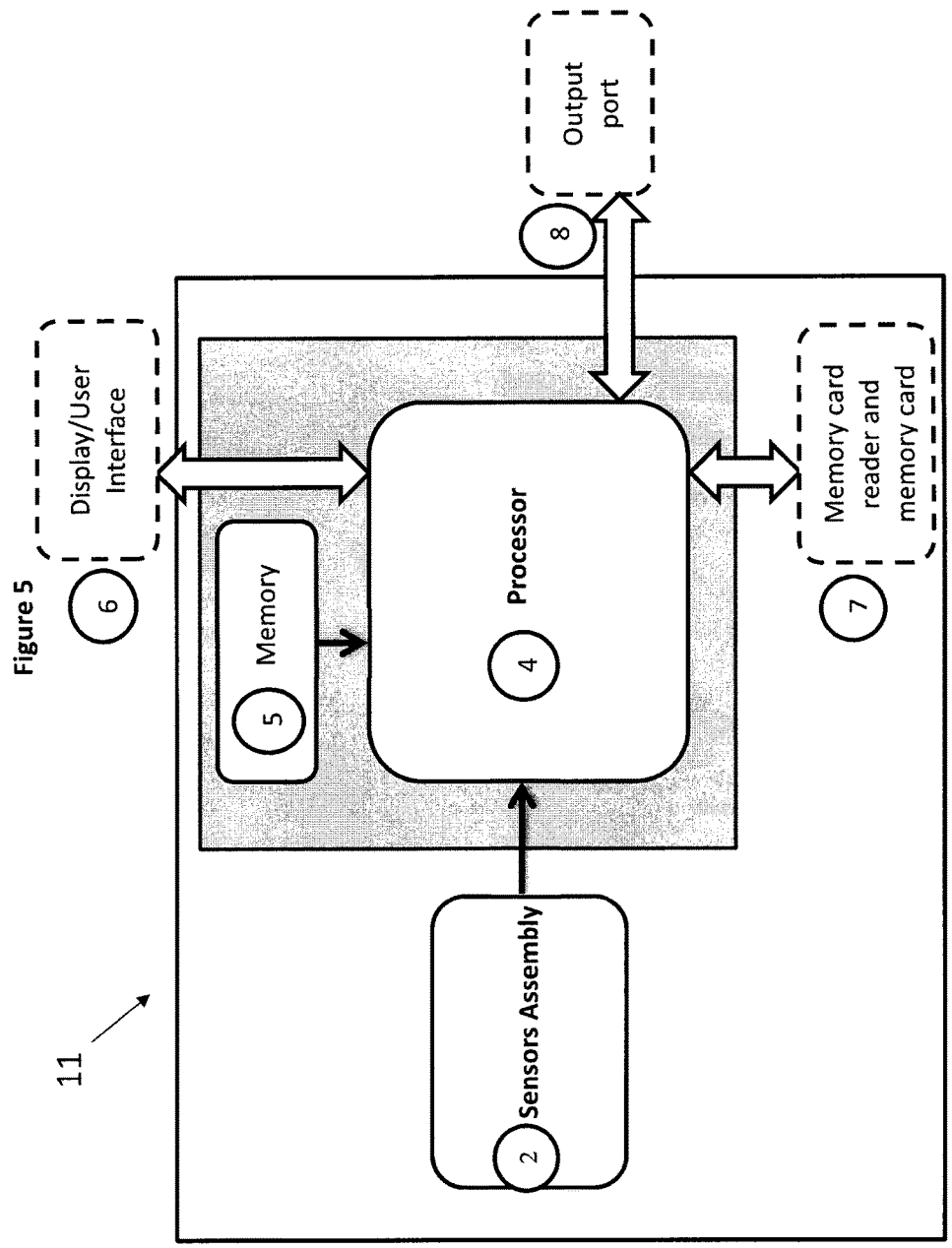
FIG. 5 is a block diagram depicting one embodiment of the device used in the model utilization phase.

Having regard to FIG. 5, the present device 11 may include a self-contained sensor assembly 2, capable of obtaining or generating "relative" or "non-reference based" readings relating to navigational information about the moving object, and producing an output indicative thereof. In one embodiment, the sensor assembly 2 may, for example, include at least one accelerometer, for measuring acceleration rates. In another embodiment, the sensor assembly 2 may, for example, include at least tri-axial accelerometer, for measuring acceleration rates. In yet another embodiment, the sensor assembly 2 may, optionally, include other self-contained sensors such as, without limitation, a gyroscope, for measuring turning rates of the of the device; a three dimensional (3D) magnetometer, for measuring magnetic field strength for establishing heading; a barometer, for measuring pressure to establish altitude; or any other sources of "relative" navigational information.

In some embodiments, the present device 11 may comprise at least one processor 4 coupled to receive the sensor readings from the sensor assembly 2. In some embodiments, the present device 11 may comprise at least one memory 5. Optionally, the device 11 may include a display or user interface 6. It is contemplated that the display 6 may be part of the device 11, or separate therefrom (e.g., connected wired or wirelessly thereto). Optionally, the device 11 may include a memory device/card 7. It is contemplated that the memory device/card 7 may be part of the device 11, or separate therefrom (e.g., connected wired or wirelessly thereto). Optionally, the device 11 may include an output port 8.

The benefit of using nonlinear model that it takes into consideration the nonlinear characteristics associated with on foot activities such as walking or running. The main drawback of the linear model is that it neglects the effect of some motion dynamics and speeds that differ among pedestrians and can cause the relation to be nonlinear. Experimental results presented later show results of the present method with a nonlinear model and the results of the known technique with a linear model.

In an embodiment of the invention the nonlinear system identification technique used is Fast Orthogonal Search (FOS); which is used to build a model that can provide an accurate varying step length regardless of the pedestrian's features and the varying human motion dynamics among pedestrians. To be able to achieve a generic mathematical model using FOS, the FOS technique should be trained with a large data set of candidate data from different pedestrians that can describe different human dynamics that vary with speed and vary among pedestrians during on foot motion activities.

FOS is a general-purpose nonlinear system identification technique that finds functional expansions using an arbitrary set of non-orthogonal candidate functions. The technique can be applied to a variety of practical problems. Applications of FOS in different research fields have shown successful detection of signals buried in short- and long-term errors. The following is a background explanation about FOS technique.

FOS is used in the system identification of a nonlinear system; the system is given by the difference equation model $$y(n)=F[y(n-1), \ldots y(n-K), x(n), \ldots x(n-L)]+e(n) \quad (1)$$

Where x(n) is the system input, y(n) is the system output while the system error is given by e(n) and n is given as n=0, ..., N where N is the number of samples.

The above equation can be represented as follows:

$$y(n) = \sum_{m=0}^{M} a_m P_m(n) + e(n) \quad (2)$$

Where $a_m$ represent the weights of the non-orthogonal candidate functions, $P_m$ is the non-orthogonal candidate functions while M is the number of candidate functions.

Fast orthogonal Search begins by building a functional expansion of y(n) using a group of orthogonal functions as follows:

$$y(n)=\Sigma_{m=0}^{M} g_m w_m(n)+e(n) \quad (3)$$

Where $g_m$ is the weight of the orthogonal functions.

$w_m$ is a set of orthogonal functions derived from $P_m$ by using Gram-Schmidt (GS) Ortho-normalization process. The GS weights $\alpha_{m,r}$ are produced by using the GS technique; these weights are used to calculate the orthogonal function $w_m$ according to the following equation:

$$\omega_m(n) = P_m(n) - \sum_{r=0}^{m-1} \alpha_{m,r} w_r(n) \quad (4)$$

The mechanism of using the FOS to identify the nonlinear system can be described in few steps; first the calculation of the $\alpha_{m,r}$ by using the GS method, and second, the calculation of the $g_m$ where it is used with the output y(n) to find the weight of the non-orthogonal candidate functions $a_m$.

The first step is the calculating of the Gram Schmidt weights $\alpha_{mr}$ by using the following equation:

$$\alpha_{mr}(n) = \frac{\overline{P_m(n) * \omega_r(n)}}{\overline{\omega_r^2(n)}} \quad (5)$$

Where the m=1, 2, 3 ... M is the index of the current term while r=0, 1, 2 ... m−1 is the index of the previous term. In order to calculate the GS weight without calculating the orthogonal functions $\omega_m$, the correlation of the candidate functions and the orthogonal functions D(m, r) is calculated according to equation (6).

$$D(m,r)=\overline{P_m(n) * \omega_r(n)} \quad (6)$$

The previous equation can be expressed by:

$$D(m, r) = \overline{P_m(n) * P_r(n)} - \sum_{i=0}^{r-1} \alpha_{ri} D(m, i)$$

One great advantage of FOS is that it does not require explicit creation of the orthogonal functions. This greatly reduces computing time. In addition, storage requirements are considerably diminished. All of this is accomplished without any degradation of the results over the basic technique to explicitly create the orthogonal functions.

From the above equations (5-6), the weights of GS can be expressed as follows:

$$\alpha_{mr}(n) = \frac{D(m, r)}{D(r, r)} \quad (7)$$

While the orthogonal functions $\omega_m$ is given as in equation (8)

$$D(m,m) = \overline{\omega_m^2(n)} \quad (8)$$

After the calculation of the Gram Schmidt weights $\alpha_{mr}$, the orthogonal functions are used to calculate and compute the orthogonal weights $g_m$. The main target of using the GS weights in the computation of the orthogonal weights is to minimize the Mean Squared Error (MSE) of the orthogonal functional expansion. The MSE is given as follows:

$$MSE = \overline{\varepsilon^2(n)} = \overline{y^2(n)} - \sum_{m=0}^{M} g_m^2 * \overline{\omega_m^2(n)} \quad (9)$$

By deriving the above equation with respect to the $g_m$ and setting its value to zero, the value of the orthogonal weights (gm) which minimize the value of the MSE is given as in equation (10)

$$g_m = \frac{\overline{y(n) * \omega_m(n)}}{\overline{\omega_m^2(n)}} \quad (10)$$

The calculation of the mean average value of the output and the orthogonal functions required to calculate the orthogonal weights $g_m$ is given in the following equation:

$$C(m) = \overline{y(n) * \omega_m(n)} = \overline{P_m(n) * y(n)} - \sum_{r=0}^{m-1} \alpha_{mr} * C(r) \quad (11)$$

Where C(m) could be solved recursively from C(0) which is equal to the mean square average of the output y(n) and equation (11) where m=1, 2, 3 . . . M. Then the value of the orthogonal weights $g_m$ is given as follows:

$$g_m = \frac{C(m)}{D(m, m)} \quad (12)$$

The MSE reduction from the addition of the $m^{th}$ term can be represented by the equation (13) where the candidate with the largest value for Q is selected as the model term, but optionally its addition to the model may be subject to its Q value exceeding a threshold level.

$$Q(M) = g_m^2 * \overline{\omega_m^2(n)} = g_m^2 * D(M,M) \quad (13)$$

By calculating the orthogonal weights $g_m$ and the GS weights $\alpha_{mr}$, the coefficients $a_m$ in equation (2) can be calculated by using the following formulas:

$$a_m = \sum_{i=m}^{M} g_i * v_i \quad (14)$$

$$v_i = -\sum_{r=m}^{i-1} \alpha_{ir} * v_r \text{ and } v_m = 1 \quad (15)$$

In the above equation the index i=m+1, 2 . . . M

By calculating the coefficients $a_m$ and having the model terms $P_m$ (n) selected, then the system in equation (2) can be represented.

Another advantage of FOS is its ability to choose both the candidate functions representing the system together with obtaining their coefficients, as opposed to some other methods that just obtains coefficients for known model structures. FOS is an efficient and effective method of system identification that is able to find accurate models of systems even from very large numbers of candidate basis functions. FOS can choose candidates from an over-complete set since it has the ability to choose the most significant candidates.

The above description is a brief background about FOS technique, which can be used for building the varying step length nonlinear model.

In some embodiments, the present method and system can use the vertical acceleration to detect steps and/or to calculate the parameters from the acceleration readings during the detected step. The vertical acceleration may be obtained by either: (i) a vertically mounted accelerometer if the application allows such a mounting; or (ii) the leveled vertical acceleration independent of the application and/or mounting. In the second case, pitch and roll angles are used in levelling the accelerometer readings to obtain the leveled vertical acceleration signal. The pitch and roll angles may be calculated from any one of the following among others: (i) gyroscopes through any one of different methods for example quaternions, (ii) accelerometers readings or averaged accelerometer readings (whether fixed-time average or moving average), or (iii) integrated navigation solution using any type of integration technique and integrating different sensors and/or systems for example some or all of the following: accelerometers, gyroscopes, magnetometers, barometer, or any navigational information updates (such as, for example, GNSS, WiFi, or any other wireless technique).

In some other embodiments, the present method and apparatus can use the magnitude of the accelerometer readings to detect steps and/or to assist in calculating the parameters from the acceleration readings during the detected step. In this latter case the gravity acceleration may or may not be removed from the magnitude depending on the usage. In all the above options in using the acceleration signal, it can be used as is, or with optional averaging, smoothing, or filtering (such as for example low pass filtering) used.

The present method and apparatus can use different parameters that represent human motion dynamics. In some embodiments, the different parameters that represent human motion dynamics used are anyone or any combination of the following: step frequency, acceleration variance during step, acceleration peak value during step, peak to peak acceleration value during step, among others. It has to be noted that the acceleration can be any of the options discussed in the previous paragraph. In one embodiment, the parameters that represent human motion dynamics used are step frequency and acceleration variance during step.

In some embodiments, the present method and apparatus can be used for step length estimation for 2D motion. In other embodiments that involve 3D motion, the present method and apparatus can be used for 3D step length estimation or for estimating the 2D projection of the step length; in such cases the different parameters that represent human motion dynamics can include some parameters related to the height or height changes. The parameters related to the height or height changes may come from one or different sources for example: (i) a barometer, (ii) height from absolute navigational information (such as GNSS), (iii) integrated height solution or navigation solution using any type of integration technique and integrating different sensors and/or systems such as for example some or all of the following: accelerometers, gyroscopes, magnetometers, barometer, or any navigational information updates (for example, GNSS, WiFi, or any other wireless technique).

In some embodiments, the inputs to the model, whether in the model-building phase (first phase) or the usage phase (second phase), are the different parameters that represent human motion dynamics. In some embodiments, the inputs to the model, whether in the model-building phase (first phase) or the usage phase (second phase), are the different parameters that represent human motion dynamics together with other inputs derived from some or all of these parameters such as (among others):
(i) different time-delayed versions of these parameters; and/or
(ii) different terms obtained by multiplying: (a) any/some/all of these parameters or their time-delayed versions by (b) any/some/all of these parameters or their time-delayed versions.

Figure 6:
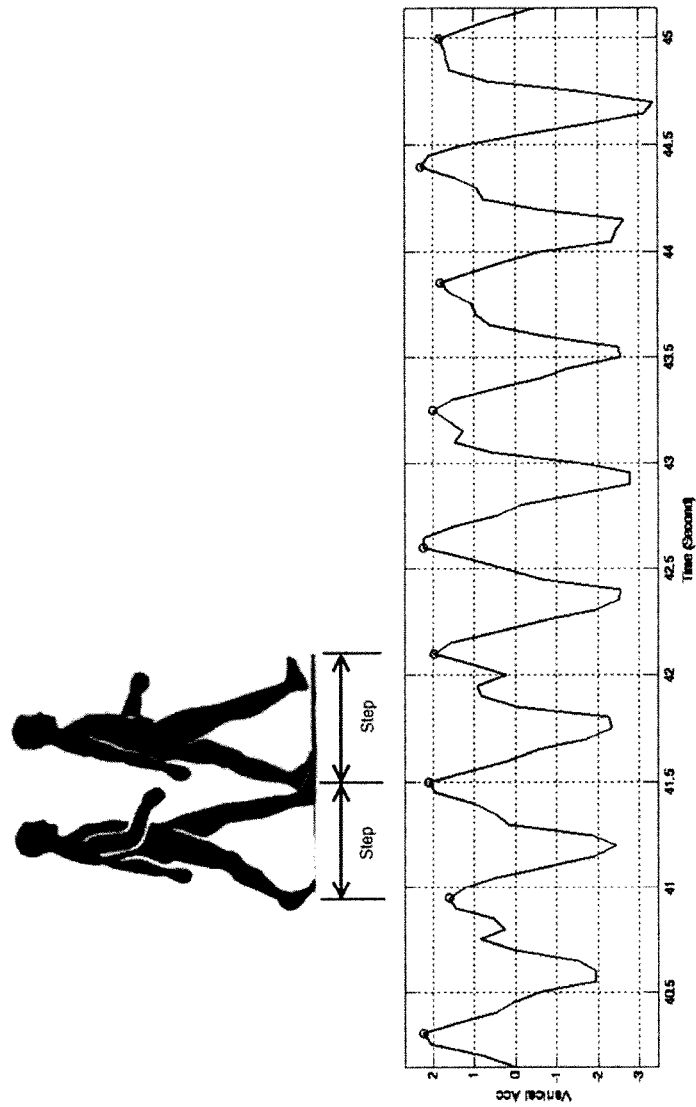
FIG. 6 is a representation of a graph and a person showing how a step is defined using peak detection technique applied on a leveled vertical acceleration signal.

In one embodiment, detecting steps from the signals discussed above is based on peak detection technique. In another embodiment, detecting steps from the signals discussed above is based on zero-crossing technique. When using the zero crossing technique and in the case the magnitude of the accelerometer readings is used, then the gravity needs to be removed from the magnitude of the accelerometer readings before applying the zero-crossing technique. FIG. 6 shows how a step is identified using peak detection technique for step detection on a leveled vertical acceleration signal. Using Peak detection technique, a step is defined as the distance between two successive positive or negative detected peaks.

During the model-building phase, a group of pedestrians' datasets (datasets consist of sensors readings) are used for building the model using the nonlinear system identification technique. In some embodiments, the group of people collecting the datasets are from different genders, and with different heights, weights, and walking and/or running styles; and this group collect the data by walking and/or running with different speeds.

In model-building, the first stage is data collection. With each step detected, a reference step length and the used parameters that represent human motion dynamics are collected, stored and then fed to the system identification technique. In the model-building phase, the reference step length can be obtained from various sources for example: (i) from an absolute navigational information source (for example GNSS or WiFi positioning), (ii) from any type of integrated navigation solution using any type of integration technique and integrating different sensors and/or systems such as for example some or all of the following: accelerometers, gyroscopes, magnetometers, barometer, or any navigational information updates (for example, GNSS, WiFi, or any other wireless technique). The used parameters that represent human motion dynamics are measured for each pedestrian with every step detected from the sensor readings in order to be used for obtaining the nonlinear model. The sensor readings can be used as is, or after optional averaging, smoothing, or filtering (such as for example low pass filtering).

During model-building, the second stage is to feed the collected data to the nonlinear system identification technique, then run it to build and obtain the nonlinear model. The step length is the target output used to build the model, and the parameters that represent human motion dynamics and/or variants from them as discussed earlier constitute the inputs to the model corresponding to the target output.

In an embodiment, FOS is chosen as an example for nonlinear system identification techniques. According to the background given above about FOS, The technique should be provided with a pool of candidate functions; the technique's main task is to search in these candidate functions, and to select a number of candidates that can build the nonlinear model for the step length as a function of different parameters representing human motion dynamics in the best way according to a minimum mean square error criterion. Searching in these candidate functions is done to obtain the best set of candidate functions capable of describing the system.

Typically, the nonlinear model is used to calculate the step length from the different parameters that represent human motion dynamics used as input to the model, wherein these parameters are obtained from sensor readings. Some example applications among others are: (i) measuring the distance traveled during an on foot activity such as walking and/or running whether with constant or varying speeds; (ii) used in Pedestrian Dead Reckoning (PDR) directly with any step detection technique and any heading source; (such PDR solution can be used solely, it can be integrated with other systems that provide absolute navigational information or with other sensors or with any integrated navigation solution using any integration technique and any sensors).

The present method and system can be used in many applications. In some embodiments, the application has the system mounted on the body of, held by, or carried by a pedestrian while moving on foot, wherein the mobility of the apparatus with respect to the pedestrian is constrained or unconstrained. The system may be tethered or non-tethered to the pedestrian body.

In some embodiments, the application using the present method and system can use: (i) the model-building only, (ii) the already obtained model only, or (iii) both model-building then model usage.

Optionally, the present method and system can be used in applications measuring the distance traveled during an on foot activity such as walking or running with constant or varying speeds.

Optionally, the present method and system can be used in Pedestrian Dead Reckoning (PDR) applications together with any step detection technique and any heading source. The heading may be calculated from any one of the following among others: (i) gyroscopes through any one of different methods for example quaternions, leveling and mathematical integration of the leveled gyroscope, mathematical integration of a vertically mounted gyroscope; (ii) integrated navigation solution using any type of integration technique and integrating different sensors and/or systems for example some or all of the following: accelerometers, gyroscopes, magnetometers, barometer, or any navigational information updates (such as, for example, GNSS, WiFi, or any other wireless technique).

Optionally, in the case the present method and system are used in a PDR solution, this PDR solution can be used solely or it can be integrated with other systems that provide absolute navigational information or with sensors or with any combination using any integration technique. Some possible examples for systems that the PDR solution can be integrated with are: inertial navigation system (INS), absolute navigational information systems (such as GNSS, WiFi, RFID, Zigbee, Cellular based localization among others), any other positioning system, combination of systems, or any integrated navigation system integrating any type of sensors or systems and using any type of integration technique. Some possible examples for integration techniques are Kalman filter, Particle filter or any other filter or estimation technique among other integration techniques.

For the model-building, in order to run the system identification technique used to build the model, any machine or device which is capable of processing can be used, wherein the model-building technique can be run and output a model for estimating the step length.

The present method and system uses at least one of the following: (i) a single axis accelerometer which is vertically mounted, or (ii) a tri-axial accelerometer (this means a triad of accelerometers). In one embodiment, the apparatus includes at least a single axis accelerometer which is vertically mounted, which may be used as the sole sensor. In another embodiment, the apparatus includes at least a tri-axial accelerometer, which may be used as the sole sensor. In another embodiment, the apparatus includes at least a tri-axial accelerometer and at least a tri-axial gyroscope, which may be used as the sole sensors. In some embodiments, in addition to the above-mentioned inertial sensors the apparatus may include additional types of sensors for example magnetometers, barometers or any other type of additional sensors, as any of the available sensors may be used. The system may also include a source of obtaining absolute navigational information (such as GNSS, WiFi, RFID, Zigbee, Cellular based localization among others), any other positioning system, or combination of systems. In embodiments that involve a 3D motion, where the step length estimation is for 3D step length estimation or for estimating the 2D projection of the step length, the system additionally includes (in addition to the above-mentioned sensor combinations) a means for measuring height or height changes, for example: (i) a barometer, or (ii) a source of obtaining absolute navigational information.

In some embodiments, the system may also include processing means. In some of these embodiments, both the sensors and/or devices in the system are in the same module or device as the processing means. In some other embodiments, the sensors and/or devices included in the system may be contained in a separate device or module other than the device or module containing the processing means, in which case the two devices or modules may communicate through a wired or a wireless mean of communication.

In some embodiments, in the model-building, the aforementioned system (whether in one or more device(s) or module(s)) may be used for any one of the following: (i) data collection and logging (including saving or storing) while the model-building technique runs on another computing machine, (ii) data reading and processing the model-building technique, (iii) data collection, logging (including saving or storing), and processing the model-building technique.

In some embodiments, in the model usage to estimate the step length, the aforementioned system (whether in one or more device(s) or module(s)) may be used for any one of the following: (i) data collection and logging (including saving or storing) while using the model for step length estimation runs on another computing machine, (ii) data reading and using the model for step length estimation, (iii) data collection, logging (including saving or storing), and using the model for step length estimation.

When the method presented herein is combined in any way with a navigation solution whether 2D or 3D, this navigation solution can use any type of state estimation or filtering techniques. The state estimation technique can be linear, nonlinear or a combination thereof. Different examples of techniques used in the navigation solution may rely on a Kalman filter, an Extended Kalman filter, a nonlinear filter such as a particle filter, or an artificial intelligence technique such as Neural Network or Fuzzy systems. The state estimation technique used in the navigation solution can use any type of system and/or measurement models. The navigation solution may follow any scheme for integrating the different sensors and systems, for example a loosely coupled integration scheme or a tightly coupled integration scheme among others. The navigation solution may utilize modeling (whether with linear or nonlinear, short memory length or long memory length) and/or automatic calibration for the errors of inertial sensors and/or the other sensors used.

Contemplated Embodiments

It is contemplated that the method and system presented above can be used with a navigation solution that may optionally utilize: automatic zero velocity periods or static period detection with possible updates and inertial sensors bias recalculations; non-holonomic updates; advanced modeling and/or calibration of inertial sensors errors; derivation of possible measurement updates from GNSS when appropriate; automatic assessment of GNSS solution quality and detecting degraded performance; automatic switching between loosely and tightly coupled integration schemes; assessment of each visible GNSS satellite when in tightly coupled mode; and finally possibly can be used with a backward smoothing module with any type of backward smoothing technique and either running in post mission or in the background on buffered data within the same mission.

It is further contemplated that the method and system presented above can also be combined with a mode of conveyance technique or a mode detection technique to establish the mode of conveyance. This enables the detection of pedestrian mode among other modes, for example driving mode. When pedestrian mode is detected, the method presented in this disclosure can be made operational.

It is further contemplated that the method and system presented above can also be used with a navigation solution that is further programmed to run, in the background, a routine to simulate artificial outages in the absolute navigational information and estimate the parameters of another instance of the state estimation technique used for the solution in the present navigation module to optimize the accuracy and the consistency of the solution. The accuracy and consistency is assessed by comparing the temporary background solution during the simulated outages to a reference solution. The reference solution may be one of the following examples: the absolute navigational information (e.g. GNSS); the forward integrated navigation solution in the device integrating the available sensors with the absolute navigational information (e.g. GNSS) and possibly with optional speed or velocity readings (for example from odometry); a backward smoothed integrated navigation solution integrating the available sensors with the absolute navigational information (e.g. GNSS) and possibly with optional speed or velocity readings (for example from odometry). The background processing can run either on the same processor as the forward solution processing or on another processor that can communicate with the first processor and can read the saved data from a shared location. The outcome of the background processing solution can benefit the real-time navigation solution in its future run (i.e. real-time run after the background routine has finished running), for example, by having improved values for the parameters of the forward state estimation technique used for navigation in the present module.

It is further contemplated that the method and system presented above can also be used with a navigation solution that is further integrated with maps (such as street maps, indoor maps or models, or any other environment map or model in cases of applications that have such maps or models available), and a map matching or model matching routine. Map matching or model matching can further enhance the navigation solution during the absolute navigation information (such as GNSS) degradation or interruption. In the case of model matching, a sensor or a group of sensors that acquire information about the environment can be used for example, laser range finders, cameras and vision systems, or sonar systems. These new systems can be used either as an extra help to enhance the accuracy of the navigation solution during absolute navigation information problems (degradation or absence), or they can totally replace the absolute navigation information in some applications.

It is further contemplated that the method and system presented above can also be used with a navigation solution that, when working either in a tightly coupled scheme or a hybrid loosely/tightly coupled option, need not be bound to utilize pseudorange measurements (which are calculated from the code not the carrier phase, thus they are called code-based pseudoranges) and the Doppler measurements (used to get the pseudorange rates). The carrier phase measurement of the GNSS receiver can be used as well, for example: (i) as an alternate way to calculate ranges instead of the code-based pseudoranges, or (ii) to enhance the range calculation by incorporating information from both code-based pseudorange and carrier-phase measurements (such enhancement is the carrier-smoothed pseudorange).

It is further contemplated that the method and system presented above can also be used with a navigation solution that relies on an ultra-tight integration scheme between GNSS receiver and the other sensors' readings.

It is further contemplated that the method and system presented above can also be used with a navigation solution that uses various wireless communication systems that can also be used for positioning and navigation either as an additional aid (i.e. will be more beneficial when GNSS is unavailable) or as a substitute for the GNSS information (e.g. for applications where GNSS is not applicable). Examples of these wireless communication systems used for positioning are, such as, those provided by cellular phone towers and signals, radio signals, digital television signals, WiFi, or Wimax. For example, for cellular phone based applications, an absolute coordinate from cell phone towers and the ranges between the indoor user and the towers may be utilized for positioning, whereby the range might be estimated by different methods among which calculating the time of arrival or the time difference of arrival of the closest cell phone positioning coordinates. A method known as Enhanced Observed Time Difference (E-OTD) can be used to get the known coordinates and range. The standard deviation for the range measurements may depend upon the type of oscillator used in the cell phone, and cell tower timing equipment and the transmission losses. WiFi positioning can be done in a variety of ways that includes but not limited to time of arrival, time difference of arrival, angles of arrival, received signal strength, and fingerprinting techniques, among others; all of the methods provide different level of accuracies. The wireless communication system used for positioning may use different techniques for modeling the errors in the ranging, angles, or signal strength from wireless signals, and may use different multipath mitigation techniques. All the above mentioned ideas, among others, are also applicable in a similar manner for other wireless positioning techniques based on wireless communications systems.

It is further contemplated that the method and system presented above can also be used with a navigation solution that utilizes aiding information from other moving devices. This aiding information can be used as additional aid (i.e. that will be more beneficial when GNSS is unavailable) or as a substitute for the GNSS information (e.g. for applications where GNSS based positioning is not applicable). One example of aiding information from other devices may be capable of relying on wireless communication systems between different devices. The underlying idea is that the devices that have better positioning or navigation solution (for example having GNSS with good availability and accuracy) can help the devices with degraded or unavailable GNSS to get an improved positioning or navigation solution. This help relies on the well-known position of the aiding device(s) and the wireless communication system for positioning the device(s) with degraded or unavailable GNSS. This contemplated variant refers to the one or both circumstance(s) where: (i) the device(s) with degraded or unavailable GNSS utilize the methods described herein and get aiding from other devices and communication system, (ii) the aiding device with GNSS available and thus a good navigation solution utilize the methods described herein. The wireless communication system used for positioning may rely on different communication protocols, and it may rely on different methods, such as for example, time of arrival, time difference of arrival, angles of arrival, and received signal strength, among others. The wireless communication system used for positioning may use different techniques for modeling the errors in the ranging and/or angles from wireless signals, and may use different multipath mitigation techniques.

It is contemplated that the method and apparatus presented above can also be used with various types of inertial sensors, other than MEMS based sensors described herein by way of example.

Without any limitation to the foregoing, the embodiments presented above are further demonstrated by way of the following examples.

EXAMPLES

Example 1—Building a Model for Walking with Different Speeds

A low-cost prototype unit was used for collecting the sensors readings to build the model. Although the present method and system does not need all the sensors and devices in this prototype unit (as discussed earlier), they are mentioned in this example just to explain the prototype used. A low-cost prototype unit consisting of a six degrees of freedom inertial unit from Invensense (i.e. tri-axial gyroscopes and tri-axial accelerometer) (MPU-6050), tri-axial magnetometers from Honeywell (HMC5883L), barometer from Measurement Specialties (MS5803), and a GPS receiver from u-blox (LEA-5T) was used.

In this example the nonlinear system identification technique used for building the nonlinear model for the step length as a function of different parameters that represent human motion dynamics is the FOS technique.

For demonstration purposes and for the sake of comparison, the present method is compared to a method from literature that considers the step length a linear function of step frequency and vertical acceleration variance using the same data collected and offline calibration for calculating the linear model parameters.

According to the previous knowledge of the step length estimation problem and how it is related to changing human dynamics during on foot motion (walking in this example), different relevant parameters were tested as possible candidate sets for the FOS technique. These sets included the following parameters (among others): step frequency, vertical acceleration variance during step, the peak to peak vertical acceleration, vertical acceleration peak value during step, acceleration magnitude variance during step, the peak to peak acceleration magnitude, acceleration magnitude peak value during step.

Eventually, the best found candidates were chosen. This pool of candidates was given to FOS technique, it included step frequency, leveled vertical acceleration variance, one delayed version of them with one sample delay, and the second order product of the previously mentioned terms. GPS was used for calculating step length (the target output) during model-building phase.

FOS technique excluded the delayed version of vertical acceleration variance, the product of the vertical acceleration variance by the delayed version of the step frequency, the product of the step frequency by its delayed version, the product of the delayed version of the step frequency by the delayed version of vertical acceleration variance, and finally, the product of the delayed version of vertical acceleration variance by itself. It is also noticed that, it gave relatively higher weights to the first and second order term of the step frequency, the vertical acceleration variance, and the product of the step frequency by the vertical acceleration variance, and relatively lower weights to the other chosen candidates in the pool.

In this demonstration example for varying speed walking, during the model-building phase the data set was collected by 17 different subject pedestrians. Different physical characteristics are considered like height, weight, gender, and age. Each subject collected data with four different walking speeds—very fast, fast, normal, and slow. Furthermore, each one of the subjects collected several datasets in each speed category, in order to have an abundance of datasets for verification. The datasets used for model-building included four datasets for each subject (each dataset with one of the aforementioned speeds, this means one very fast, one fast, one normal, and one slow).

The obtained model is meant to be suitable for the different walking styles of people with different speeds.

After the nonlinear model is built by FOS, the model is tested using a large amount of data, which consists of both: (i) a large number of completely new data to the model, which itself contains other data collected by the same pedestrians who collected the data used in model-building, and a data set collected by new pedestrians where none of their data was used in the model-building phase; and (ii) data used in the building phase of the model just for verification.

For the sake of comparison the same data sets used in both building the FOS model are used for offline calculation of the linear model coefficients using the linear regression approach (this is a technique available in the prior art and presented for the sake of demonstrating the enhancement of FOS nonlinear model).

Example 2—Using Varying Step Length Model for Walking with Different Speeds

A low-cost prototype unit was used for using, demonstrating and validating the varying step length model (obtained by FOS) for walking with different speeds. Although the present method and apparatus does not need all the sensors and devices in this prototype unit (as discussed earlier), they are mentioned in this example just to explain the prototype used. A low-cost prototype unit including a six degrees of freedom inertial unit from Invensense (i.e. tri-axial gyroscopes and tri-axial accelerometer) (MPU-6050), tri-axial magnetometers from Honeywell (HMC5883L), barometer from Measurement Specialties (MS5803), and a GPS receiver from u-blox (LEA-5T) was used.

The proposed method and apparatus are tested through a large number of trajectories from different pedestrians with different walking speeds (several pedestrians are different from those used for model-building) to demonstrate how the proposed step length estimation method and apparatus can handle different walking dynamics.

A comparison is held between the present method for varying step length estimation using FOS-built model as an example of the nonlinear system identification technique used in building the nonlinear model and the linear regression model from literature that estimates step length as a linear function of step frequency and vertical acceleration variance during the step. Both models were built using the same model-building data. The results using the nonlinear model built by FOS is compared against the results using the linear regression model.

The ultimate way to demonstrate the step length models is to look at the positioning results from PDR solutions each of which is using one of the models. The same PDR solution is applied with the same step detection technique to make sure that the number of steps detected is equal, and also the same heading source is provided to both PDR solutions utilizing the two models. Therefore the only difference between the compared solutions is due to the different step length estimation model used.

For demonstration purposes, three example walking trajectories among those collected are presented below to show how the proposed method and apparatus are able to provide a generic model for step length that varies with different pedestrians with different walking speeds and how it can perform more accurately than the prior art.

Figure 7:
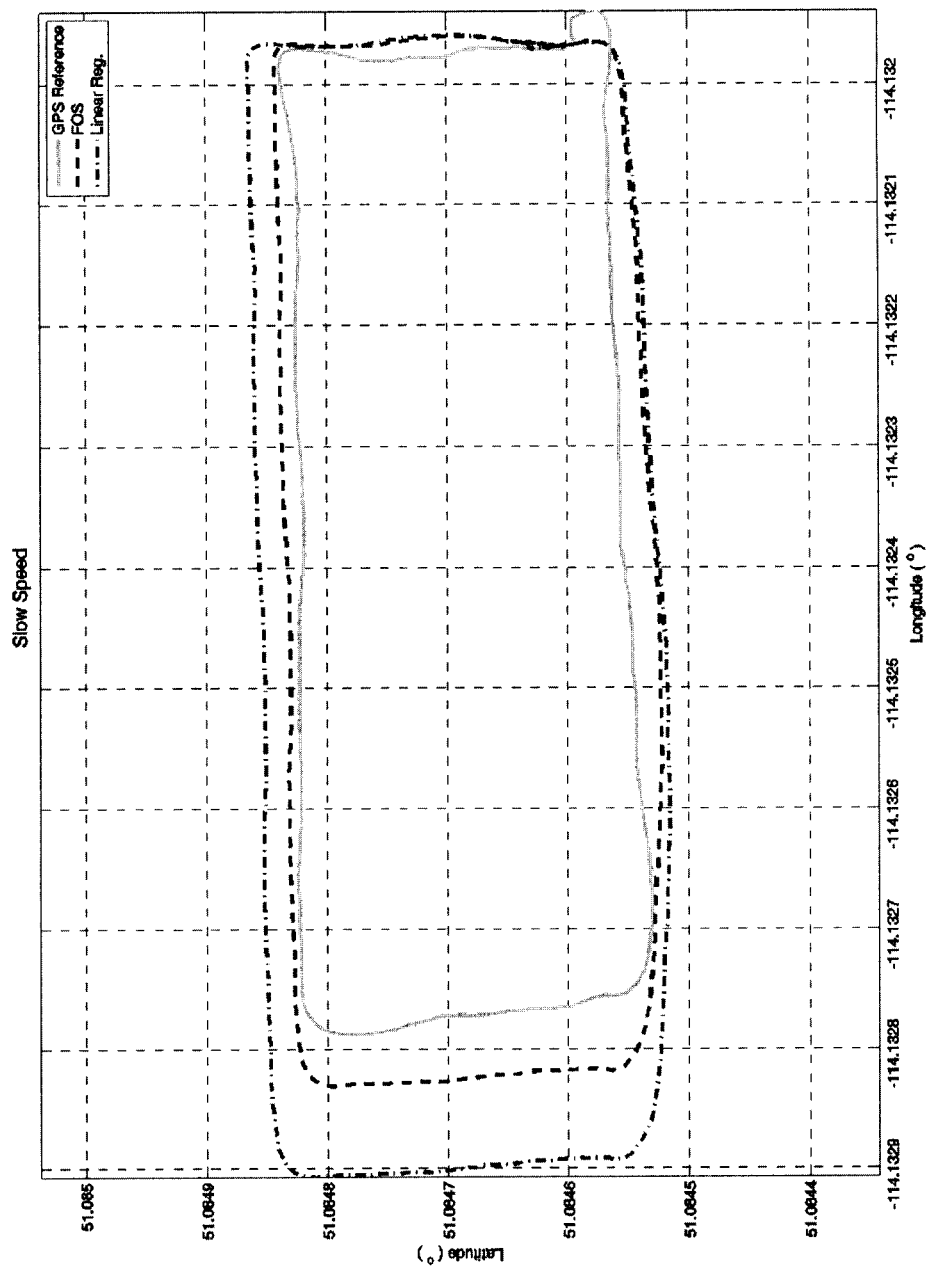
FIG. 7 is a graph showing positioning results for a slow walking speed trajectory from an example data set.
Figure 8:
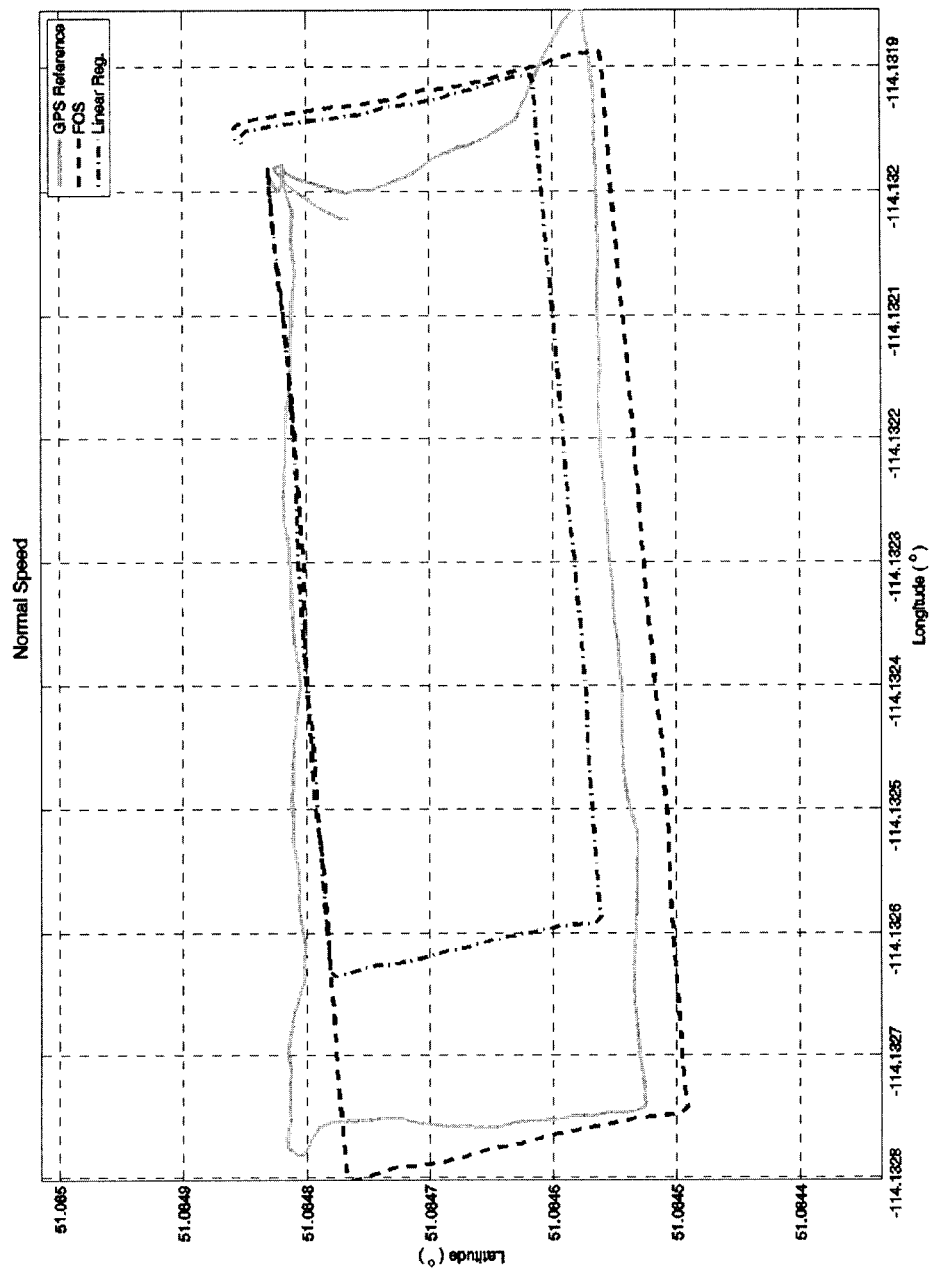
FIG. 8 is a graph showing positioning results for a normal walking speed trajectory from an example data set.
Figure 9:
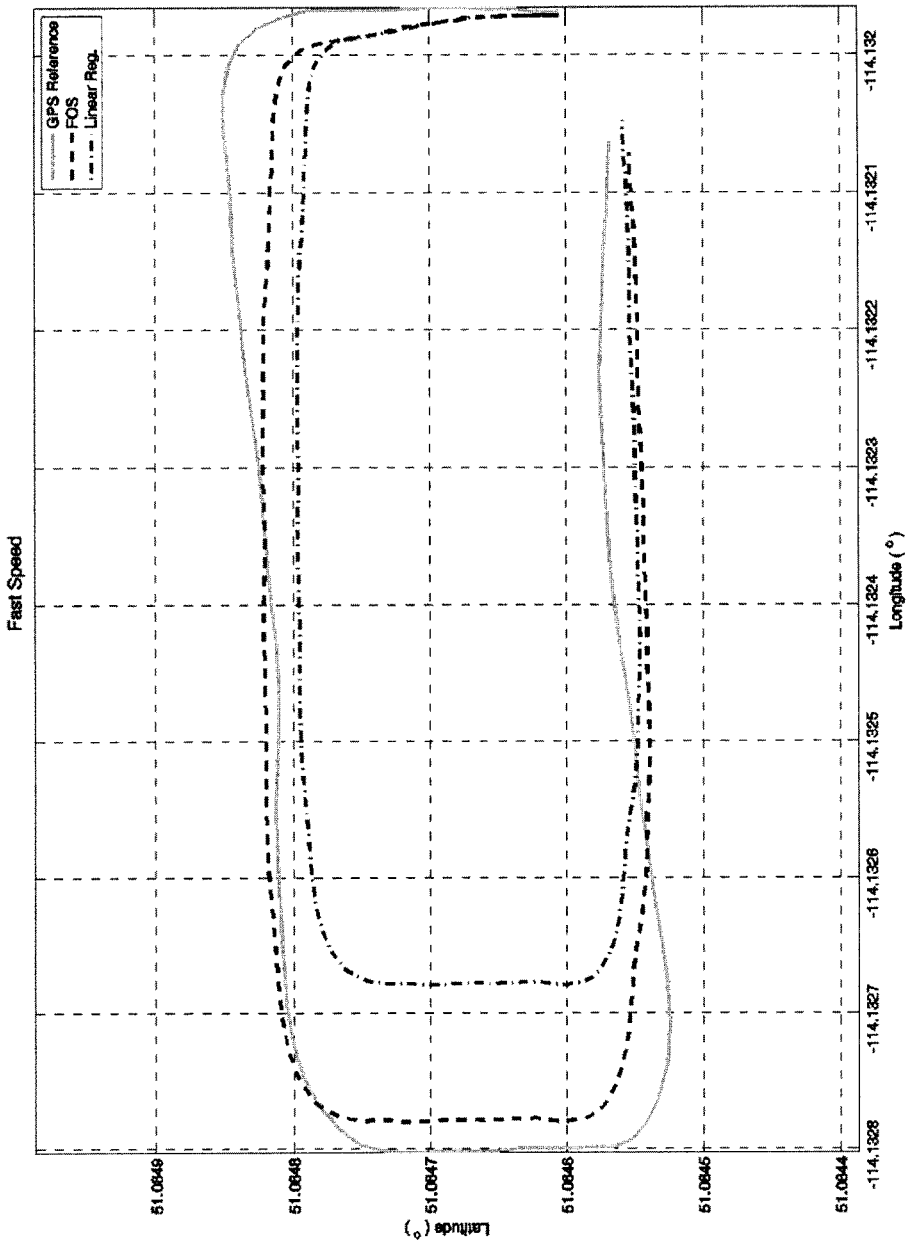
FIG. 9 is a graph showing positioning results for a fast walking speed trajectory from an example data set.

In this example a rectangular trajectory is used to compare between the two methods where GPS is used as a reference. In FIG. 7, FIG. 8, and FIG. 9, the GPS solution is shown in solid line, the PDR with FOS model results is shown in solid line with circle marker, and the PDR with linear regression model results is shown in dash-dot line.

In FIG. 7, the slow walking speed result is shown. The PDR result shows how the proposed method of using nonlinear model generated from FOS is closer to the reference, on the other hand, the linear regression model overestimates the step length which results in a bigger PDR trajectory compared to the reference.

In FIG. 8, the normal walking speed result is shown. The PDR result shows how the proposed method of using nonlinear model generated from FOS is closer to the reference, on the other hand, the linear regression model underestimates the step length which results in a smaller PDR trajectory compared to the reference.

In FIG. 9, the fast walking speed result is shown. The PDR result shows how the proposed method of using nonlinear model generated from FOS is closer to the reference, on the other hand, the linear regression model underestimates the step length which results in a smaller PDR trajectory compared to the reference.

These results demonstrate that the step length estimated from the nonlinear model generated by FOS is more accurate than the one estimated from linear regression model.

Example 3—Building a Model for Running with Different Speeds

A low-cost prototype unit was used for collecting the sensors readings to build the model. Although the present method and system does not need all the sensors and devices in this prototype unit (as discussed earlier), they are mentioned in this example just to explain the prototype used. A low-cost prototype unit including a six degrees of freedom inertial unit from Invensense (i.e. tri-axial gyroscopes and tri-axial accelerometer) (MPU-6050), tri-axial magnetometers from Honeywell (HMC5883L), barometer from Measurement Specialties (MS5803), and a GPS receiver from u-blox (LEA-5T) was used.

In this example the nonlinear system identification technique used for building the nonlinear model for the step length as a function of different parameters that represent human motion dynamics is the FOS technique.

For demonstration purposes and for the sake of comparison, the present method is compared to a prior art method that considers the step length a linear function of step frequency and vertical acceleration variance using the same data collected and offline calibration for calculating the linear model parameters.

According to the previous knowledge of the step length estimation problem and how it is related to changing human dynamics during on foot motion (running in this example), different relevant parameters were tested as possible candidate sets for the FOS technique. These sets included the following parameters (among others): step frequency, vertical acceleration variance during step, the peak to peak vertical acceleration, vertical acceleration peak value during step, acceleration magnitude variance during step, the peak to peak acceleration magnitude, acceleration magnitude peak value during step.

Eventually, the best found candidates were chosen. This pool of candidates was given to FOS technique were step frequency, leveled vertical acceleration variance, one delayed version of them with one sample delay, and the second order product of the previously mentioned terms. GPS was used for calculating step length (the target output) during model-building phase.

FOS technique excluded the delayed version of vertical acceleration variance, the product of the vertical acceleration variance by the delayed version of the step frequency, the product of the step frequency by its delayed version, the product of the delayed version of the step frequency by the delayed version of vertical acceleration variance, and finally, the product of the delayed version of vertical acceleration variance by itself. It is also noticed that the FOS technique gave relatively higher weights to the first and second order term of the step frequency, the vertical acceleration variance, and the product of the step frequency by the vertical acceleration variance, and relatively lower weights to the other chosen candidates in the pool.

In this demonstration example for varying speed running, during the model-building phase the data set was collected by 10 different pedestrian subjects. Different physical characteristics are considered like height, weight, gender, and age. Each subject collected data with six different running speeds—extreme fast, very fast, fast, normal, slow, and very slow. Furthermore, each one of the subjects collected several datasets in each speed category, in order to have an abundance of datasets for verification. The datasets used for model-building included four datasets for each subject (each dataset with one of the aforementioned speeds, meaning one very fast, one fast, one normal, and one slow).

The obtained model is meant to be suitable for the different running styles of people with different speeds.

After the nonlinear model is built by FOS, the model is tested using a large amount of data, which includes both: (i) a large amount of completely new data to the model, which itself contains other data collected by the same users who collected the data used in model-building, and a data set collected by new users where none of their data was used in the model-building phase; and (ii) data used in the building phase of the model just for verification.

For the sake of comparison the same data sets used in both building the FOS model are used for offline calculation of the linear model coefficients using linear regression approach (this is a technique available in the prior art and presented for the sake of demonstrating the enhancement of FOS nonlinear model).

Example 4—Using Varying Step Length Model for Running with Different Speeds

A low-cost prototype unit was used for using, demonstrating and validating the varying step length model (obtained by FOS) for running with different speeds. Although the present method and system does not need all the sensors and devices in this prototype unit (as discussed earlier), they are mentioned in this example just to explain the prototype used. A low-cost prototype unit including a six degrees of freedom inertial unit from Invensense (i.e. tri-axial gyroscopes and tri-axial accelerometer) (MPU-6050), tri-axial magnetometers from Honeywell (HMC5883L), barometer from Measurement Specialties (MS5803), and a GPS receiver from u-blox (LEA-5T) was used.

The proposed method and apparatus are tested through a large number of trajectories from different pedestrians with different running speeds (several users are different from those used for model-building) to demonstrate how the proposed step length estimation method and apparatus can handle different running dynamics.

A comparison is held between the present method for varying step length estimation using FOS-built model as an example of the nonlinear system identification technique used in building the nonlinear model and the prior art linear regression model that estimates step length as a linear function of step frequency and vertical acceleration variance during the step. Both models were built using the same model-building data. The results using the nonlinear model built by FOS is compared against the results using the linear regression model.

A way to demonstrate the step length models is to look at the positioning results from PDR solutions, each of which is using one of the models. The same PDR solution is applied with the same step detection technique to make sure that the number of steps detected is equal, and also the same heading source is provided to both PDR solutions utilizing the two models. Therefore the only difference between the compared solutions is due to the different step length estimation model used.

For demonstration purposes, six example running trajectories among those collected are presented below to show how the proposed method and apparatus are able to provide a generic model for step length that varies with different pedestrians with different running speeds and how it can perform more accurately than prior art solutions.

Figure 10:
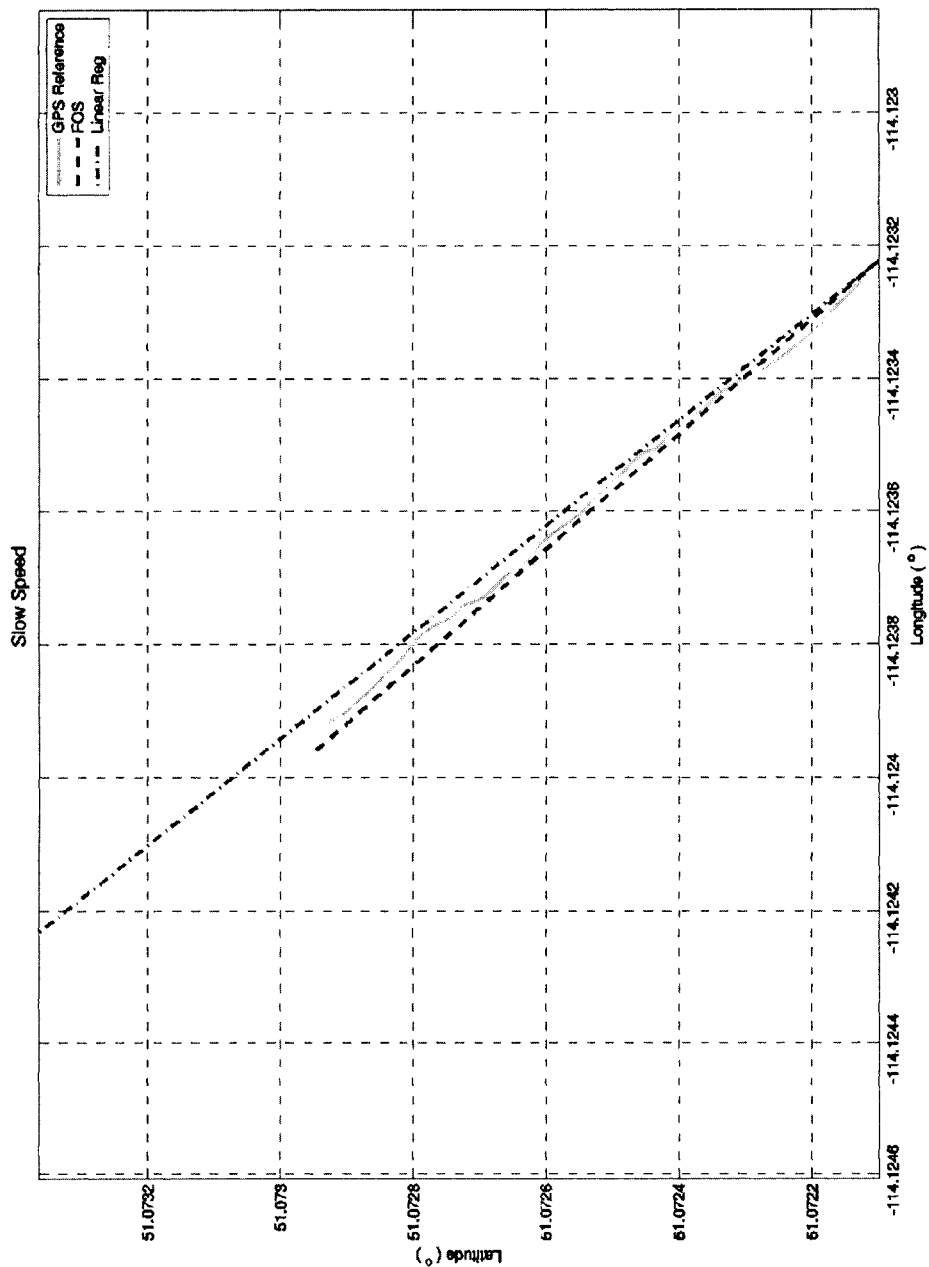
FIG. 10 is a graph showing positioning results for a slow running speed trajectory from an example data set.
Figure 11:
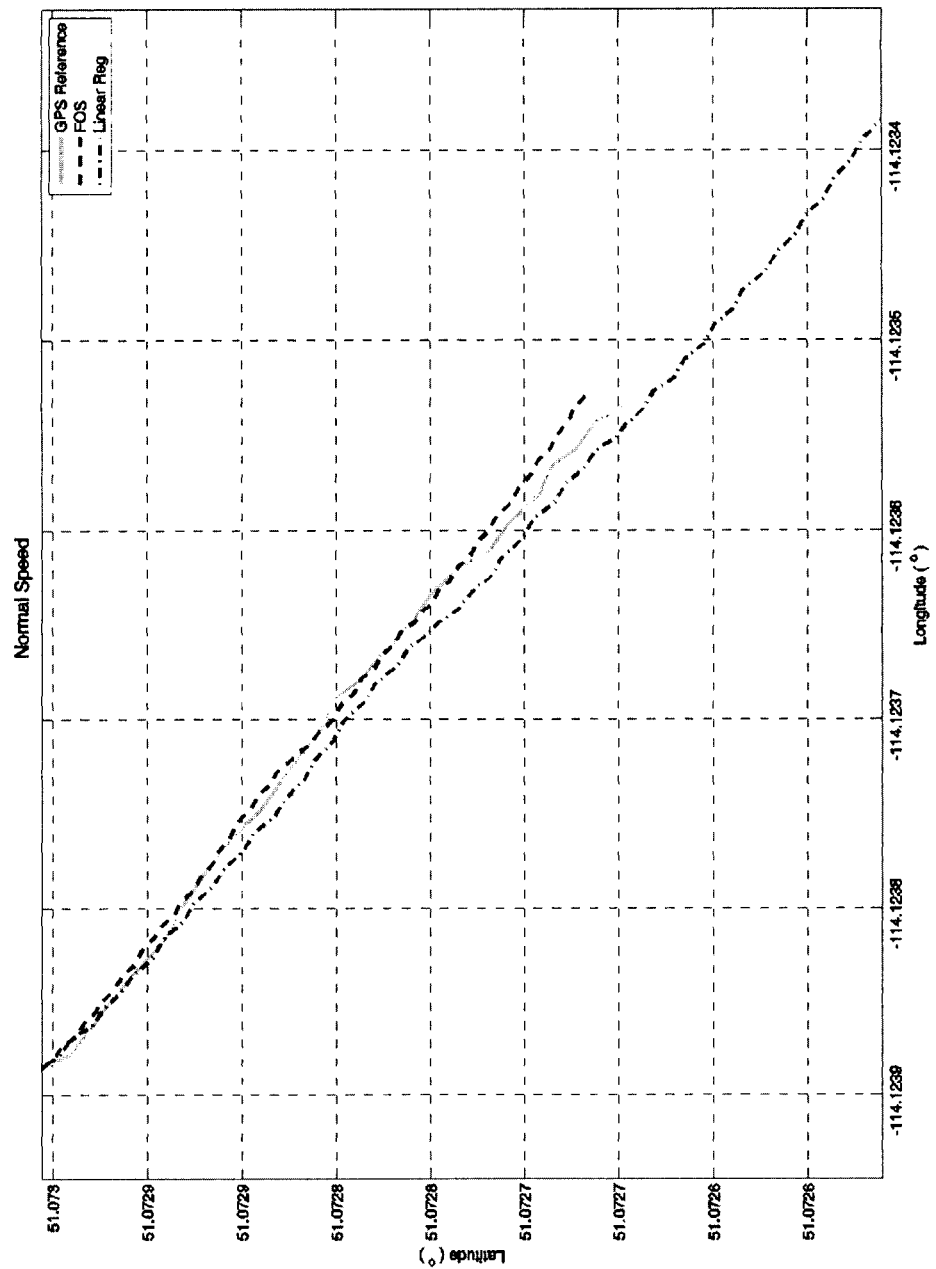
FIG. 11 is a graph showing positioning results for a normal running speed trajectory from an example data set.
Figure 12:
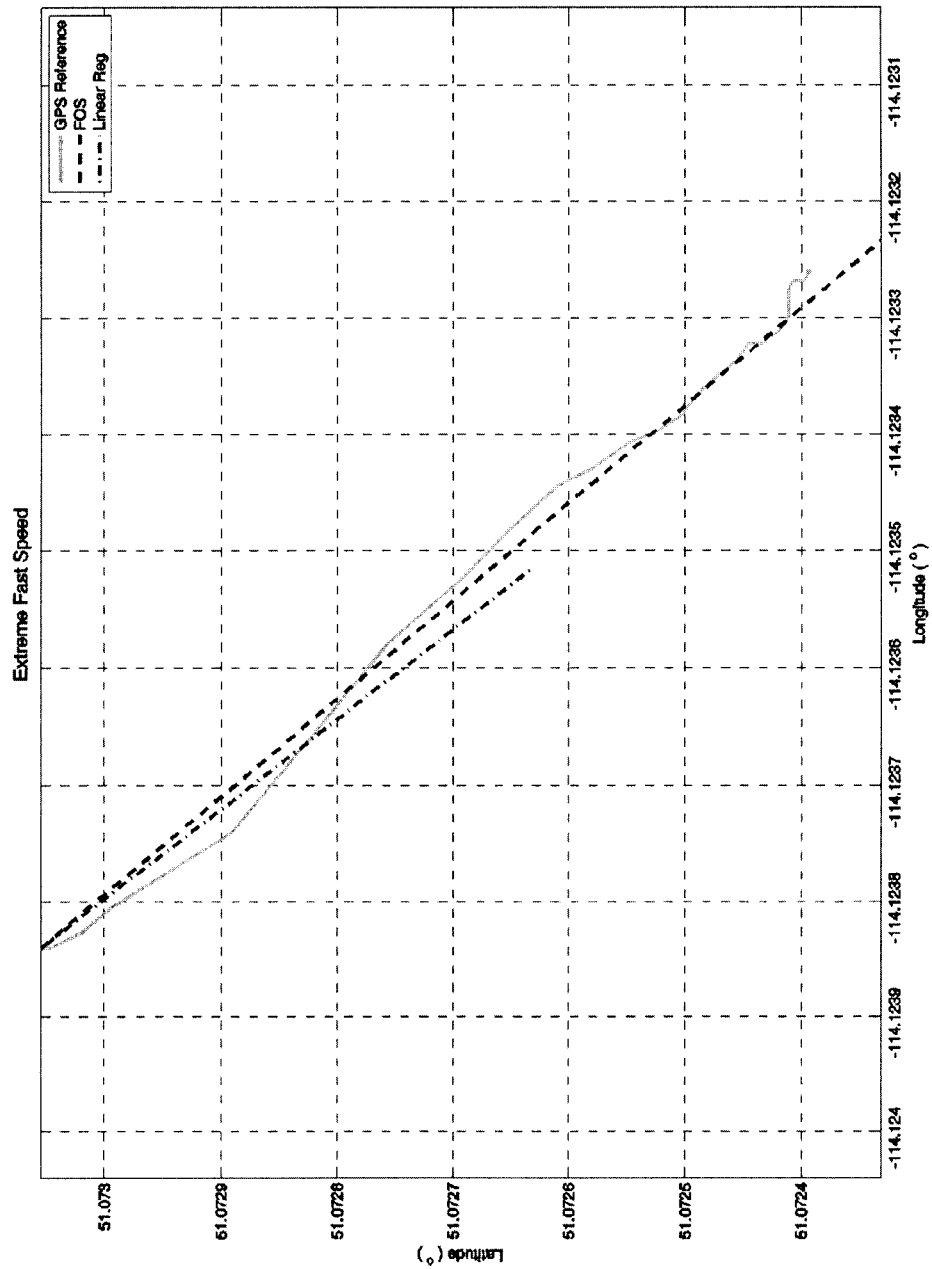
FIG. 12 is a graph showing positioning results for an extreme fast running speed trajectory from an example data set.

In this example a straight line trajectory is used to compare between the two methods where GPS is used as a reference. In FIG. 10, FIG. 11, and FIG. 12, the GPS solution is shown in solid line, the PDR with FOS model results is shown in solid line with circle marker, and the PDR with linear regression model results is shown in dash-dot line.

In FIG. 10, the slow running speed result is shown. The PDR result shows how the proposed method of using nonlinear model generated from FOS is closer to the reference, on the other hand, the linear regression model again overestimates the step length which results in a longer PDR trajectory compared to the reference.

In FIG. 11, the normal running speed result is shown. The PDR result shows how the proposed method of using nonlinear model generated from FOS is closer to the reference, on the other hand, the linear regression model overestimates the step length which results in a longer PDR trajectory compared to the reference.

In FIG. 12, the extreme fast running speed result is shown. The PDR result shows how the proposed method of using nonlinear model generated from FOS is closer to the reference, on the other hand, the linear regression model underestimates the step length which results in a shorter PDR trajectory compared to the reference.

These results demonstrate that the step length estimated from the nonlinear model generated by FOS is more accurate than the one estimated from linear regression model.

The embodiments and techniques described above may be implemented as a system or plurality of systems working in conjunction, or in software as various interconnected functional blocks or distinct software modules. This is not necessary, however, and there may be cases where these functional blocks or modules are equivalently aggregated into a single logic device, program or operation with unclear boundaries. In any event, the functional blocks and software modules implementing the embodiments described above, or features of the interface can be implemented by themselves, or in combination with other operations in either hardware or software, either within the device entirely, or in conjunction with the device and other processor enabled devices in communication with the device, such as a server.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

The embodiments in which an exclusive property or privilege is claimed are defined as follows:

1. A method for estimating varying step length for on foot motion of a pedestrian, the method comprising:
   a) providing a device moveable with the pedestrian, the device positionable in any orientation, wherein the device comprises a sensor assembly, and wherein the sensor assembly comprises at least one sensor, the at least one sensor configured to provide sensor readings;
   b) detecting steps from the sensor readings;
   c) obtaining parameters that represent human motion dynamics from the sensor readings for the detected steps; and
   d) using the parameters that represent human motion dynamics to:
      i) build an improved, previously unknown step length model for on foot motion using a nonlinear system identification technique,
      ii) utilize an improved step length model to estimate step length for on foot motion, wherein the step length model was previously unknown and was built using a nonlinear system identification technique, or
      iii) build an improved, previously unknown step length model for on foot motion using a nonlinear system identification technique and utilize the step length model built to estimate step length.

2. The method of claim 1,
   wherein detecting steps from the sensor readings comprises obtaining sensor readings for a plurality of pedestrians and running a step detection technique on the obtained sensor readings to detect steps; and
   wherein building the step length model using the nonlinear system identification technique to estimate step length comprises:
      obtaining a reference step length for each detected step,
      feeding the parameters that represent human motion dynamics and the reference step length to the nonlinear system identification technique and
      running the system identification technique to build a model to estimate a step length from the parameters that represent human motion dynamics.

3. The method of claim 1,
   wherein detecting steps from the sensor readings comprises obtaining the sensor readings and running a step detection technique on the sensor readings to detect a step; and
   wherein utilizing the step length model built using the nonlinear system identification technique comprises passing the parameters that represent human motion dynamics to the step length model and estimating an output step length from the model.

4. The method in any one of claim 1, 2, or 3, wherein the method is operable with the device untethered to the pedestrian.

5. The method in any one of claim 1, 2, or 3, wherein the method is operable with the device tethered to the pedestrian.

6. The method in any one of claim 1, 2, or 3, wherein the nonlinear system identification technique is Fast Orthogonal Search.

7. The method in any one of claim 1, 2, or 3, wherein the at least one sensor in the sensor assembly comprises an accelerometer.

8. The method of claim 7, wherein parameters that represent human motion dynamics are one or more of the following: step frequency, acceleration variance during step, acceleration peak value during step, or peak to peak acceleration value during step.

9. The method in any one of claim 1, 2, or 3, wherein the at least one sensor in the sensor assembly comprises a tri-axial accelerometer.

10. The method of claim 9, wherein parameters that represent human motion dynamics are one or more of the following: step frequency, acceleration variance during step, acceleration peak value during step, or peak to peak acceleration value during step.

11. A system for estimating varying step length for on foot motion of a pedestrian, the system comprising:
  a) a device moveable with the pedestrian, the device in any orientation, the device comprising:
    i) an assembly of sensors comprising at least one sensor, the at least one sensor configured to provide sensor readings; and
    ii) a receiver for receiving absolute navigational information about the device from an external source, and producing an absolute navigational information output; and
  b) a processor, coupled to receive the sensor readings and the absolute navigational information output, and operative to:
    i) detect steps from the sensor readings;
    ii) obtain parameters that represent human motion dynamics from the sensor readings for the detected steps; and
    iii) use the parameters that represent human motion dynamics to:
      (A) build an improved, previously unknown step length model for on foot motion using a nonlinear system identification technique,
      (B) utilize an improved step length model to estimate step length for on foot motion, wherein the model was previously unknown and was built using a nonlinear system identification technique, or
      (C) build an improved, previously unknown step length model for on foot motion using a nonlinear system identification technique and utilize the step length model to estimate step length.

12. The system of claim 11, wherein the processor is further operative to
  obtain the sensor readings for a plurality of pedestrians,
  obtain a reference step length for each detected step,
  feed the parameters that represent human motion dynamics and the reference step length to the nonlinear system identification technique and
  run the system identification technique to build the model to estimate the step length from the parameters that represent human motion dynamics.

13. The system of claim 11, wherein the processor is further operative to
  pass the parameters that represent human motion dynamics to the step length model and estimate the output step length from the model, wherein the step length model was built using the system identification technique.

14. The system of any one of claim 11, 12, or 13, wherein the device is untethered to the pedestrian.

15. The system of any one of claim 11, 12, or 13, wherein the device is tethered to the pedestrian.

16. The system of any one of claim 11, 12, or 13, wherein the at least one sensor in the sensor assembly comprises an accelerometer.

17. The system of any one of claim 11, 12, or 13, wherein the at least one sensor in the sensor assembly comprises a tri-axial accelerometer.

18. The system of any one of claim 11, 12, or 13, wherein the processor is within the device.

19. The system of any one of claim 11, 12, or 13, wherein the processor is not within the device.

* * * * *